United States Patent [19]

Pratt et al.

[11] 4,454,875

[45] Jun. 19, 1984

[54] OSTEAL MEDICAL STAPLE

[75] Inventors: Clyde R. Pratt, Somis; Roger G. Carignan, Ventura, both of Calif.

[73] Assignee: Techmedica, Inc., Camarillo, Calif.

[21] Appl. No.: 368,622

[22] Filed: Apr. 15, 1982

[51] Int. Cl.³ .............................................. A61F 5/04
[52] U.S. Cl. .............................. 128/92 B; 128/334 R
[58] Field of Search ..................... 128/92 B, 334, 335, 128/337; 411/457, 456, 458, 459, 460

[56] References Cited

FOREIGN PATENT DOCUMENTS 335439 9/1930 United Kingdom ................ 411/457

OTHER PUBLICATIONS

The Journal of Bone & Joint Surgery, No. 821, Barbed Staple, vol. 52-A, No. 8, Dec. 1970.
Vitallium Surgical Appliances Catalogue, No. 6985-3, De Palma Staples, 1964.

Primary Examiner—John D. Yasko
Attorney, Agent, or Firm—Cislo, O'Reilly & Thomas

[57] ABSTRACT

An osteal medical staple of unique configuration having a cross-bar portion defining gripping surfaces by which the staple may be securely and rigidly held by a driver tool or the like, wherein the staple has depending leg portions flaring outwardly a predetermined amount such that regardless of the size of the staple a discrete, constant spread or flaring is obtained once same is implanted in bone or the like, and wherein loosening or reversal of the driven staple is all but eliminated by reason of the triangular, in cross-section, legs of the staple wherein two of the sides have retention barbs thereby insuring complete and total fixation while the curvilinear surfaces of the cross-bar portion of the staple insure a minimum of damage to soft tissue surrounding the bone with which the staple is utilized. Securing spikes on the undersurface of the cross-bar portion of the staple, as well as the integral metal construction of same provide for a substantially inert, high-quality, high-performance staple particularly suitable for the attachment of soft tissue such as ligaments or tendons to bone.

17 Claims, 6 Drawing Figures

OSTEAL MEDICAL STAPLE

BACKGROUND OF THE INVENTION

This invention pertains to medical staples of the type that are utilized by orthopedic surgeons for the repair of broken bones and the like, and the attachment of natural and artificial ligaments in reconstructive surgery and the like.

The prior art has suggested various types of staples, some of which have been specifically fabricated for association with staple drivers and the like, and one such staple is shown in the prior art patent to Griggs, U.S. Pat. No. 4,263,903.

The staple of the present invention overcomes many of the shortcomings of prior art staples. It is capable of retaining soft tissue and bone in a rigid and secure manner wherein the staple is provided with various features to facilitate the end function and result for which it is intended.

The medical staple used in soft tissue and bone fixation should be one that provides uniformity and constancy of results regardless of its area of application. A medical staple must be one that is easily driven through soft tissue and bone with a minimum of damage, yet providing a maximum of retention in securing so as to accomplish the job for which it is intended. The medical staple of the type utilized with staple holders or drivers must also provide suitable and adequate gripping surfaces by which the staple may be held for implantation and removal, if necessary.

The staple of the invention meets all of the foregoing criteria in that a medical staple is provided which is integrally fabricated or biologically inert metal, such as stainless steel, titanium,cobolt-chromium-molybdenum or the like, and has a cross-bar portion selectively configured to accommodate various driving and holding devices and further, has depending legs which are triangular-shaped in cross-section wherein the interior or base of the triange is smooth while the remaining intersecting legs of the triangle are provided with chevron-shaped ridges or barbs, insuring secure retention once the medical staple has been set or implanted.

The medical staple has slightly outwardly flaring legs so that a uniform, constant spread of the legs is obtained during the implantation or driving process through bone and the like. To facilitate driving, tapered termini to the legs is provided, and to insure retention of soft tissue, retaining and holding spikes are provided on the undersurface of the cross-bar portion of the staple.

OBJECTS AND SUMMARY OF THE INVENTION

It is an object of the invention to provide an osteal medical staple of unique configuration and design.

It is another, important object of the invention to provide a medical staple of metal, integral construction wherein a cross-bar portion has depending, slightly outwardly flaring legs.

It is another, even further, more specific object of the invention to provide a medical staple of the type for association with soft tissue and bone wherein the staple has slightly outwardly flaring legs, having barb-like means thereon to insure secure retention within bone and the like.

It is another, even further, more important specific object of the invention to provide a medical staple having an integral construction, comprising a cross-bar portion having spaced, depending legs of triangular cross-section configuration, wherein the termini of the legs are tapered for ease of implantation and wherein barbed means are provided to insure secure retention within bone structure.

It is another, even further, more specific and illustrative object of the invention to provide a medical staple for particular association with soft tissue and bone wherein the medical staple has filleted and curvilinear surfaces so as to decrease soft tissue trauma upon insertion of the medical staple in bone structure and the like.

It is another, even further and more specific illustrative object of the invention to provide a medical staple having an integral construction comprising a cross-bar portion of specific shape and having depending triangular-shaped legs having barbed means thereon wherein the undersurface of the cross-bar is provided with soft tissue retaining spikes or the like.

It is another, further illustrative and specific object of the invention to provide a medical staple having depending legs of slightly outwardly flaring relationship wherein regardless of the size of the staple or the distance between legs, the implanted spread or flaring of the legs is constant and uniform.

It is another, even further, specific and detailed object of the invention to provide a medical staple having outwardly flaring legs having barb-like retaining means thereon which is easily secured within the bone structure and soft tissue and wherein loosening or undesired backout of the staple is substantially diminished.

It is another, even further important object of the invention to provide a medical staple having a cross-bar portion having rounded edges and broad surface contact so as to minimize injury to soft tissues being held down by the staples; and to soft tissues riding over the top of the cross-bar.

It is still another, even more specific object of the invention to provide a medical staple having rigid triangular legs with tapered or chiseled termini which facilitate insertion and driving into bone structure and wherein the legs are tapered so as to create compression forces upon driving and setting of the medical staple in bone structure by way of the forced flaring of the legs.

In an exemplary embodiment, the invention is directed to a staple comprising the combination of an integral member having a cross-bar portion defining gripping means by which said staple may be grasped. The cross-bar portion has curvilinear or rounded termini or edges terminating in depending and extending legs, each of the legs flaring outwardly from the cross-bar portion wherein the legs have barbed means thereon to inhibit withdrawal movement of the staple once same has been positioned in its fixation environment.

These and further objects of the invention will become apparent from the hereinafter following commentary taken in conjunction with the drawing.

BRIEF DESCRIPTION OF THE DRAWING

FIG. 5 is a view taken along the line 6—6 of FIG. 4.

DESCRIPTION OF THE BEST EMBODIMENTS CONTEMPLATED

Figure 1:
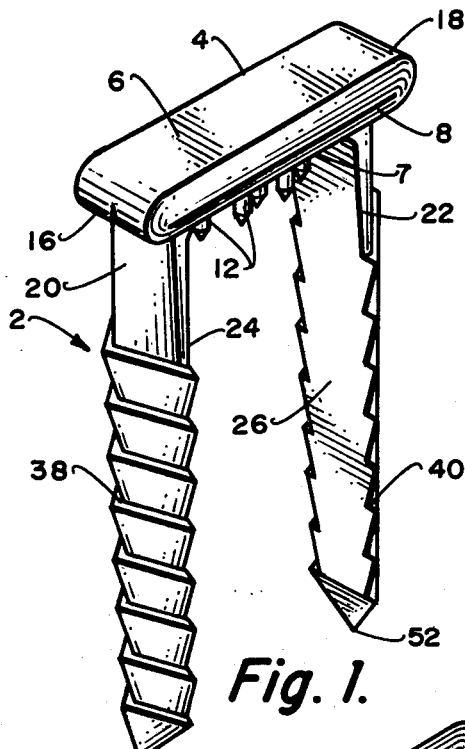
FIG. 1 is a perspective view of one of the embodiments of the medical staple of the invention.

While the medical staple of the invention will be described as it specifically relates to those embodiments of the invention depicted in the drawing, it should be understood that various size and various legged staples are contemplated, i.e., where the cross-bar is longer, wider, or the like, than that shown, and where the depending legs are multiple and spaced apart further or closer, or longer or shorter, depending upon the ultimate field of application. The parameters of the inventive staple, as will become apparent to those of ordinary skill in the art, may be applied to all such different sizes of devices, and while a specific design or configuration to the cross-bar of the medical staple will be disclosed, those of ordinary skill in the art will at once recognize that the attributes and essence of the invention may be applied to medical staples of different design so long as the basic medical staple features, as will be described, are adhered to.

Referring to the figures of drawing wherein like numerals of reference designate like elements throughout, two of five or six different sizes of staples are illustrated in this particular case being of stainless steel (of surgical type) or of a cobalt-chromium-molybdenum alloy or of titanium metal. The staple 2 is shown as comprising a cross-bar portion 4, having an upper surface 6 and a lower surface 7 and having a somewhat rectangular configuration with lateral projecting surfaces 8 and 10, somewhat hexagonal-shaped, providing gripping surfaces by which the staple 2 may be securely and rigidly held by means of a staple holder device not shown.

The staple 2 is of integral construction and the undersurface 7 is provided with spaced, projecting spikes 12, in this particular instance five in number, and having tapered points 14 intended to secure soft tissue, ligaments or the like as is commonplace in orthopedic surgery. It will be noted that the lateral surfaces 8 and 10 are somewhat curvilinear as opposed to having sharp, breaking edges or surfaces to thereby prevent undue traumatization to surrounding soft tissue when the staple 2 is being driven or implanted. The cross-bar portion 4 terminates in termini 16 and 18 similarly curvilinear or rounded so as to prevent soft tissue destruction.

The termini 16 and 18 have depending and extending legs 20 and 22, the interior surfaces 24 and 26 of which are smooth, while the adjacent surfaces are barbed or the like.

The depending legs 20 and 22 are triangular-like in cross-section with the smooth surfaces 24 and 26 forming the base of the triangle while the opposed legs 30 and 32 of leg 20 and 34 and 36 of leg 22 are configured with chevron-shaped ridges 38 and 40 respectively, forming barbed means for insuring secure retention of the staple 2 once the staple has been driven into bone structure or the like.

The ridges 38 and 40 form a 45-degree angle with respect to a horizontal datum 44. The legs 20 and 22 are filleted or rounded as at 46 and 48 where same intersect the undersurface 7 of cross-bar portion 4. The depending legs 20 and 22 terminate in chiseled or pointed ends 50 and 52 respectively, the ends being tapered at about a 45-degree angle to facilitate driving of the staple 2 through tissue and bone.

The legs 20 and 22 are slightly tapered with respect to each other and flare outwardly to insure compression retention of the staple once same is driven through soft tissue and into bone or the like structure. The legs flare outwardly about 2-6 degrees from a vertical and in the illustration shown, about 3 degrees from a vertical datum 60.

The relationship of the triangular cross-section of the legs 20 and 22 to the chevron-shaped ridges 38 and 40 in conjunction with the flare or outwardly spreading of the legs is such that regardless of the size of the staple 2, the legs 20 and 22 always flare outwardly a uniform and constant amount, that amount being about 0.200 of an inch. Thus, regardless of the distance between the legs 20 and 22 and regardless of the length of the legs a driven and set staple will flare outwardly and take a set of a constant dimension, which along with the barbed means on the legs 20 and 22 make the staple 2 of the invention about 3 times more difficult to remove than prior art medical staples not having the features of the staple 2.

The staple 2 with its broad cross-bar portion 4 and the configuration thereof, and in particular, the setting spikes 12 insure less trauma to surrounding soft tissue while being set or driven and at the same time insures that soft tissue will be retained where wanted for a sufficiently long time for tissue fixation to take place. The outwardly protruding gripper sides 8 and 10 insure the ability to securely grasp and hold the medical staple either by hand or with a staple driver during the setting or removing process. The barb-like arrangement of the triangular-shaped legs 20 and 22 insure against vertical or lateral pullout of the staple 2 from the bone structure with which it is associated. The chiseled or tapered points 50 and 52 of legs 20 and 22 along with the slight outwardly flaring of said legs provide ease of setting of the staple and also create compression forces between the staple legs contributing to decrease of the potential for vertical backout of the medical staple 2 and compresses bone fragments which facilitates bone healing.

Figure 4:
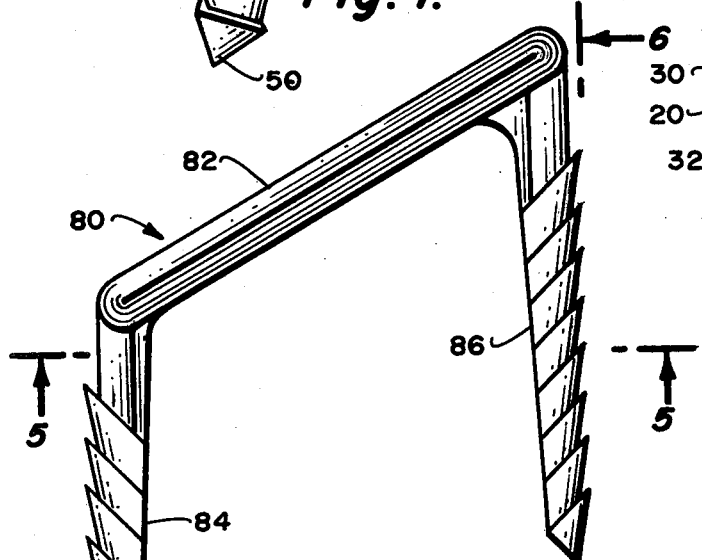
FIG. 4 is a side elevational view of another embodiment of the medical staple of the invention.
Figure 5:
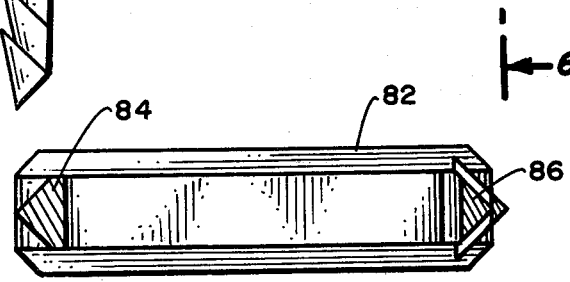
FIG. 5 is a view taken along the line 5—5 of FIG. 4.
Figure 6:
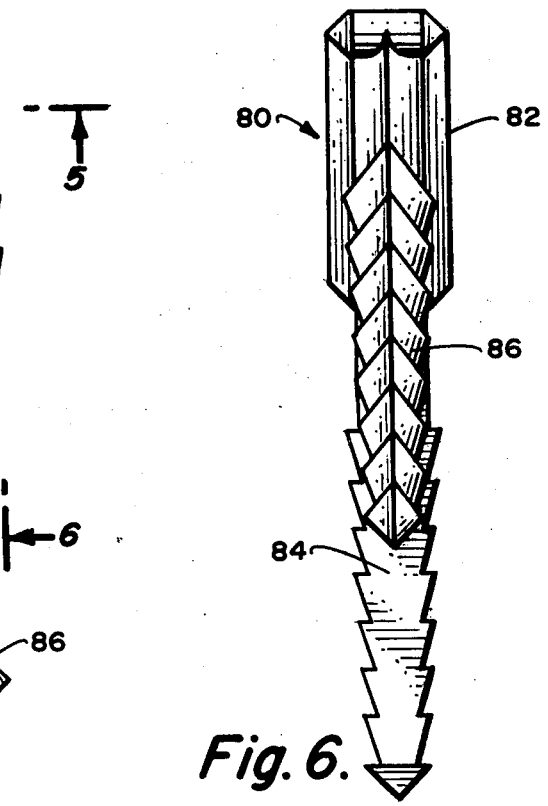

Referring now to FIGS. 4–6, inclusive, another embodiment of the invention is depicted which has all of the salient features alluded to hereinbefore for the staple 2 but differs only in certain aspects, as will be seen.

Herein the staple 80 has a cross-bar portion 82 fulfilling all of the parameters set forth for the cross-bar 4 of medical staple 2, but in this instance being of slightly elongated configuration for hybrid utilization in particular end uses.

The staple 80 has depending leg 84 with spaced depending leg 86. In all other particulars with the exception of the slant or askewness of the cross-bar 82 relative to legs 84 and 86 and the difference in spacing of legs 84 and 86, all other aspects of the staple 80 coincide with those aspects heretofore described with respect to staple 2 with the obvious exception, of course, of the deletion of spikes 12 on the undersurface of cross-bar 82.

Since those of ordinary skill in the art will at once recognize the field of use and the details of construction of the staple 80 in reference to the previous description of the staple 2, further description of the staple 80 will not be delved into.

Figure 2:
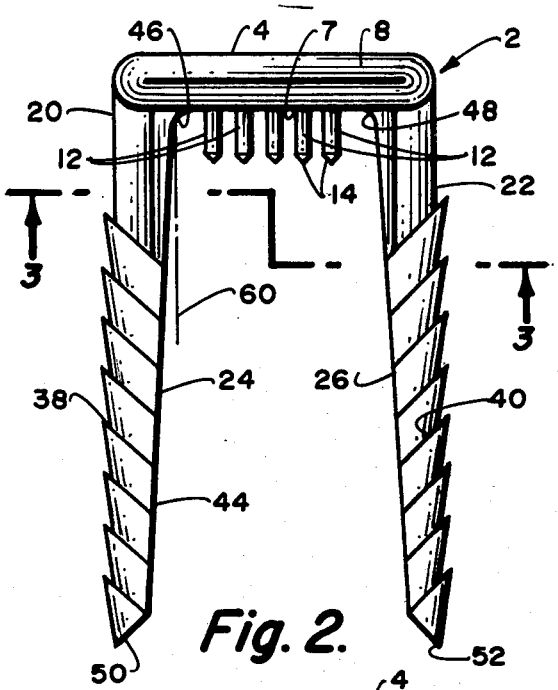
FIG. 2 is a side elevational view of the staple illustrated in FIG. 1.
Figure 3:
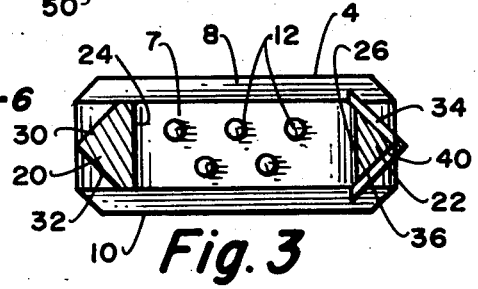
FIG. 3 is a view taken along the line 3—3 of FIG. 2.

The cross-bar of the staples of the invention may be of any size, but the most versatile sizes are those ranging from 1 to 2 centimeters with various increments in between wherein the legs, measured from the underside or surface of the cross-bar, may be between 1–4 centimeters depending upon end use function desired. In the embodiment of the invention illustrated in FIGS. 1–3, inclusive, the spikes 12 may be eliminated, as those of ordinary skill in the art will recognize. Likewise, while a specific hybrid staple is illustrated in FIG. 4, other various sizes and shapes will present themselves depending upon field application and desirability imposed by the orthopedic surgeon. However, the various attributes of the invention and their application to medical staples having different gripping surfaces, or indeed, barbed means on the legs, will be apparent to those of ordinary skill in the art. Thus, there has been disclosed a medical staple particularly adapted for association with soft tissue and bone structure wherein the staple provides for controlled leg bending and reduced backout and tissue injury problems. The polygonal cross-bar of the staple having rounded edges and broad tissue contact area helps distribute the load and thus reduces potential for soft tissue injury. The configuration of the broad cross-bar also insures sufficient gripping of the staple either by hand or with a staple holder device. The triangular-shaped barbs eliminate backout potential from either vertical or lateral force applications while the surfaces between the cross-bar and the legs being of filleted or oblique configuration eliminates sharp edges and right angles which may cut or tear soft tissue.

The rigid, triangular legs of the staple with the chisel points facilitate driving and setting of the staple, and the reinforced corners at the juncture of cross-bar and depending legs reduces uncontrolled staple leg bending while the taper or flare on the legs creates compression upon driving of the staple.

While there are various changes and modifications other than those briefly alluded to hereinbefore that will occur to thos of ordinary skill in the art, all such changes and modifications are intended to be encompassed by the appended claims.

We claim:

1. An osteal medical staple comprising the combination: an integral member having a cross-bar portion of a substantially rectangular configuration with a substantially flat lower surface providing a broad tissue contact area, termini at opposite ends thereof, and lateral protuberances at opposite sides thereof defining gripping means by which said staple may be grasped; a depending leg extending from said lower surface of said cross-bar adjacent each of said termini, the width of each of said legs being less than the distance between lateral protuberances on opposite sides of each cross-bar portion, such that the opposite lateral surfaces of said legs are spaced inwardly from said lateral proturberances, and being flared outwardly from said cross-bar portion; and barbed means on each of said depending legs adapted to inhibit withdrawal movement of said staple once same has been positioned in its fixation environment.

2. The staple in accordance with claim 1 wherein said legs are triangular in shape in cross-section.

3. The staple in accordance with claim 2 wherein said barbed means are located on the exterior of said legs.

4. The staple in accordance with claim 3 wherein the interior surface of each leg is smooth and in cross-section forms the base of the triangle of said triangular cross-section.

5. The staple in accordance with claim 4 wherein the terminus of each leg opposite said cross-bar portion is tapered.

6. The medical staple in accordance with claim 5 wherein said barbed means are formed by chevron-like ridges formed in the exterior surface of each of said depending legs.

7. The medical staple in accordance with claim 6 wherein a portion of said depending legs adjacent said cross-bar is smooth.

8. The staple in accordance with claim 7 wherein said staple is of metal construction and the relationship of flare of said depending legs and tapered end thereof is such as to cause said staple to assume a discrete and about constant, fixed spread regardless of size, said spread being about 0.200 inch.

9. The medical staple in accordance with claim 7 wherein the undersurface of said bar is provided with spaced spikes and the intersection of said undersurface with said depending legs is filleted.

10. The medical staple in accordance with claim 9 wherein each of said legs flare outwardly about 2°–6° from vertical measured from a vertical datum intersecting and normal to the undersurface of said cross-bar portion.

11. The medical staple in accordance with claim 10 wherein said flare is about 3°.

12. The medical staple in accordance with claim 11 wherein the taper at said terminus of each leg opposite said cross-bar portion is about 45° with respect to a horizontal datum.

13. The medical staple in accordance with claim 12 wherein each of said chevron-like ridges form about a 45° angle with respect to a horizontal datum.

14. The medical staple in accordance with claim 1 wherein said legs are of equal length and said cross-bar portions forms an angle of about 5°–45° with respect to a horizontal datum.

15. An osteal medical staple comprising the combination: an integral member having a cross-bar portion defining gripping means by which said staple may be gripped, said cross-bar portion having curvilinear termini and lateral protuberances; and at least one depending leg having a triangular, in cross-section, configuration, two sides of said depending leg having barbed means thereon to inhibit withdrawal movement of said staple.

16. The staple in accordance with claim 15 which additionally includes at least an additional depending leg spaced from said at least one depending leg of like configuration, each of said legs being in flared relationship to each other and said cross-bar.

17. An osteal medical staple comprising the combination: an integral member having a cross-bar portion defining gripping means by which said staple may be grasped, said cross-bar portion having curvilinear termini, each of which terminate in a depending leg extending therefrom, each of said legs being triangular in shape in cross-section and flaring outwardly from said cross-bar portion; and barbed less than the distance between the lateral protuberances on cross-bar and they are not spaced inwardly from the ends of the positioned in its fixation environment.

* * * * *

UNITED STATES PATENT AND TRADEMARK OFFICE
CERTIFICATE OF CORRECTION

PATENT NO. : 4,454,875

DATED : June 19, 1984

INVENTOR(S) : Clyde R. Pratt, et al

It is certified that error appears in the above-identified patent and that said Letters Patent is hereby corrected as shown below:

Column 6, line 53, claim 17 should be corrected as follows:

An osteal medical staple comprising the combination: an integral member having a cross-bar portion defining gripping means by which said staple may be grasped, said cross-bar portion having curvilinear termini, each of which terminate in a depending leg extending therefrom, each of said legs being triangular in shape in cross-section and flaring outwardly from said cross-bar portion; and barbed "less than the distance between the lateral protuberances on cross-bar and they are not spaced inwardly from the ends of the" (means on each of said depending legs adapted to inhibit withdrawal movement of said staple once same has been) positioned in its fixation environment.

Signed and Sealed this

Eighteenth Day of December 1984

[SEAL]

Attest:

Attesting Officer

GERALD J. MOSSINGHOFF

Commissioner of Patents and Trademarks